United States Patent
Santana et al.

(10) Patent No.: US 11,285,427 B2
(45) Date of Patent: Mar. 29, 2022

(54) SYSTEMS AND METHODS FOR ACETYLENE PURIFICATION

(71) Applicant: TRANSFORM MATERIALS LLC, Riviera Beach, FL (US)

(72) Inventors: Alexander Olson Santana, Tequesta, FL (US); James Nathan Ashcraft, Jupiter, FL (US); David S. Soane, Palm Beach, FL (US)

(73) Assignee: Transform Materials LLC, Riviera Beach, FL (US)

( * ) Notice: Subject to any disclaimer, the term of this patent is extended or adjusted under 35 U.S.C. 154(b) by 193 days.

(21) Appl. No.: 16/877,630

(22) Filed: May 19, 2020

(65) Prior Publication Data

US 2020/0368670 A1 Nov. 26, 2020

Related U.S. Application Data

(60) Provisional application No. 62/850,233, filed on May 20, 2019.

(51) Int. Cl.
*C07C 7/00* (2006.01)
*B01D 53/04* (2006.01)
(Continued)

(52) U.S. Cl.
CPC ..... *B01D 53/0462* (2013.01); *B01D 53/0446* (2013.01); *B01J 20/18* (2013.01);
(Continued)

(58) Field of Classification Search
CPC .. C07C 7/12; C07C 11/02; C07C 7/13; C07C 11/24; C07C 11/30; C07C 11/22;
(Continued)

(56) References Cited

U.S. PATENT DOCUMENTS

| 3,060,247 A | 10/1962 | Wolfram et al. |
| 3,683,592 A | 8/1972 | Kamm et al. |

(Continued)

FOREIGN PATENT DOCUMENTS

WO 2020041597 A1 2/2020

*Primary Examiner* — Sharon Pregler
(74) *Attorney, Agent, or Firm* — Elmore Patent Law Group, P.C.; Mahreen Chaudhry Hoda; Carolyn S. Elmore

(57) ABSTRACT

The invention includes methods for removing higher acetylenes from a gaseous stream that includes a hydrogen fraction and a non-hydrogen fraction, wherein the gaseous stream includes less than about 4% in total of diacetylene and vinylacetylene, where the method includes the following steps: (i) an adsorption that passes the gaseous stream at a preselected superficial linear gas velocity across an adsorption bed supported within an enclosure, the adsorption bed containing a crystalline porous ceramic adsorbent to adsorb the higher acetylenes onto the adsorbent, thereby producing a saturated adsorption bed and a purified gaseous stream including less than about 25 ppm of diacetylene that regenerates the saturated adsorbent bed by passing a regeneration gas across the saturated adsorption bed to desorb the higher acetylenes retained thereupon, thereby producing a regenerated adsorbent bed and a contaminated gas stream bearing the higher acetylenes; and (iii) a purging step that removes the contaminated gas stream from the enclosure. The invention also includes systems for removing diacetylene and vinylacetylene from a hydrogen-dominant acetylene-hydrogen gaseous stream.

24 Claims, 5 Drawing Sheets

(51) Int. Cl.
  *B01J 20/18* (2006.01)
  *C07C 7/13* (2006.01)
  *B01J 20/28* (2006.01)

(52) U.S. Cl.
  CPC .......... *C07C 7/13* (2013.01); *B01D 2253/116* (2013.01); *B01D 2253/306* (2013.01); *B01D 2253/308* (2013.01); *B01D 2257/7022* (2013.01); *B01D 2259/40007* (2013.01); *B01D 2259/40043* (2013.01); *B01J 20/28061* (2013.01); *B01J 20/28083* (2013.01); *B01J 20/28085* (2013.01)

(58) Field of Classification Search
  CPC ........... C07C 2/80; C07C 7/148; C07C 7/152; C07C 7/163; C07C 11/00; C07C 11/28; C07C 2/78; B01D 53/0462; B01D 2257/108; B01D 2259/40007; B01D 2259/40043; B01D 53/04; B01D 53/0446; B01D 53/047; B01D 53/14; B01D 53/1487; B01D 53/46
  See application file for complete search history.

(56) References Cited

U.S. PATENT DOCUMENTS

| | | |
|---|---|---|
| 3,870,482 A | 3/1975 | Walker et al. |
| 7,393,993 B1 * | 7/2008 | Kanazirev ............... C07C 7/148 585/809 |
| 2020/0062591 A1 | 2/2020 | Soane et al. |
| 2020/0063040 A1 | 2/2020 | Soane et al. |

* cited by examiner

SYSTEMS AND METHODS FOR ACETYLENE PURIFICATION

RELATED APPLICATION

This application claims the benefit of U.S. Provisional Application No. 62/850,233 filed May 20, 2019. The entire contents of this application are incorporated by reference herein.

FIELD OF THE APPLICATION

This application relates to systems and methods for removing higher acetylenes from gaseous acetylene streams.

BACKGROUND

When acetylene is generated from a hydrocarbon source, the kinetics of acetylene formation typically lead to the formation of higher acetylene byproducts, such as the $C_4$ byproducts diacetylene and vinylacetylene. As used herein, the term "higher acetylenes" refers at least to alkynes containing 3 and 4 carbon atoms, although it can also be applied to all gaseous alkynes and to gaseous aromatics. These higher acetylenes can polymerize in situ, fouling downstream equipment and solvents. Moreover, these higher acetylenes are highly dangerous: in particular they have high explosion hazards. The presence of higher acetylenes in acetylene streams also reduces the commercial value of the acetylene stream for many uses, because the higher acetylenes can participate in chemical reactions along with the acetylene, leading to an undesirable mixture of chemical products. For all of these reasons, such higher acetylenes are desirably removed from acetylene streams in order to produce a pure acetylene product.

For many industrial applications, the easiest way to remove the higher acetylenes is to pass the acetylene stream containing them through a solvent at an early stage of the process. Higher acetylenes have a higher solubility than acetylene in a number of solvents, so that they can be preferentially absorbed. Typically, the acetylene stream containing higher acetylenes is introduced at low pressure into a small amount of solvent such as water, methanol, liquid ammonia, dimethylformamide (DMF), N-methylpyrrolidinone (NMP), benzene, or another organic solvent. However, acetylene is also soluble in these solvents, albeit less so than the higher acetylenes. Therefore, during the solvent-based purification, some acetylene is co-absorbed with the higher acetylenes, leading to acetylene loss from the process gas. Additionally, concentrating higher acetylenes in a liquid media can present additional safety hazards.

Because removing all the higher acetylenes through exposure to a single solvent can lead to unacceptable acetylene loss, alternative, multi-step separation methods such as caustic and sulfuric acid scrubbing can be employed to reduce the amount of acetylene loss while still removing the higher acetylenes adequately. For example, certain higher acetylenes (e.g., diacetylene and other hydrocarbon contaminants such as other $C_4$ compounds and aromatics) can be removed in an initial solvent-containing step, while vinylacetylene (another higher acetylene compound) continues to accompany the acetylene in the gas stream, requiring subsequent removal via a process like vacuum stripping in order to produce a sufficiently pure acetylene product. Cost-effective solvent-based acetylene purification remains challenging though, because of the tendency for acetylene loss during the separation processes and because of the complexities of the systems needed to remove the higher acetylenes adequately.

In many industries, gas or liquid streams are purified by adsorption instead of solvent-based absorption. An adsorber system includes a substance, called an adsorbent, that preferentially removes certain molecules, called the adsorbate, from the fluid stream. By segregating the molecules that preferentially adsorb, the adsorbent removes them from the fluid stream. The adsorbed molecules can be contaminants to be eliminated from the fluid stream, or they can be the products to be recovered from the fluid stream.

The adsorbent can be a material having a differential affinity for a target compound as compared with other compounds in the fluid stream. Alternatively, the adsorbent can differentiate between or among molecules on the basis of molecular size or other physical property. Adsorbents may also be selected because of other, auxiliary properties, such as their stability in extreme temperatures or pressures, their stability in pH extremes, or their stability in the presence of certain organic solvents. Adsorbents, however, have a limited capacity, becoming saturated with the target molecules over time. To restore the adsorbent to an efficient state, regeneration must be carried out; regeneration is a process that removes the adsorbate from the adsorbent surface (i.e., desorption) and reconditions the adsorbent surface.

As an example of an adsorber system, a temperature swing adsorber (TSA) can be used to remove molecules of interest. In a TSA, the desorption step is accomplished by applying heat to the saturated adsorbent and optionally flowing a regeneration gas over it. Due to the heat and the difference in the partial pressures of the adsorbate on the surface of the adsorbent material and the regeneration gas, the adsorbate can be driven off into the regeneration gas stream. The adsorbent bed must then be cooled after desorption to become usable for another adsorption cycle.

Adsorbents, while efficient in removing target molecules, can become saturated quickly, requiring recurring cycles of regeneration so that they can continue to function. This makes adsorption systems expensive to operate, especially when they are exposed to large amounts of contaminants. Adsorption systems have not typically been employed for acetylene purification processes because commercial acetylene streams contain high concentrations of contaminants that can readily saturate the adsorbents. Moreover, because of the recurring need for adsorbent regeneration, TSA systems commonly use multiple vessels so that a subset of the system's vessels is adsorbing the target molecule, while another subset of vessels is regenerating the adsorbate. The need for complex adsorption systems introduces capital costs as well as operating costs.

Without being bound by theory, it is understood that hydrocarbon separation by adsorption proceeds by taking advantage of differential intermolecular attraction forces of the various hydrocarbons to the adsorbent material. Additionally, without being bound by theory, it is understood that certain hydrocarbons condense preferentially on the surface of the adsorbent because they have lower vapor pressures than other molecules. Large differences between the mass of a hydrocarbon contaminant versus the product hydrocarbon in the gas stream allow for long windows of time for contaminant adsorption while the product hydrocarbons pass through the adsorbent bed, allowing for efficient and economical separation of contaminants from the product gas stream. For example, the difference in mass between methane and benzene allows these two gases to be readily separated via adsorption at an industrial scale. Separating a hydrocarbon contaminant from a product hydrocarbon is much more difficult when the contaminant and the product are close in mass and have similar adsorption properties. Under these circumstances, the window of adsorption time to separate the two similar gases is small; with a small adsorption window, more frequent adsorption regeneration is required to maintain its separation efficacy, and/or larger amounts of adsorbent can be required. Adsorption can thus become cost-prohibitive as a separation technique.

Moreover, adsorption processes involving acetylene typically focus on removing acetylene from other hydrocarbon products, with acetylene being an impurity in the hydrocarbon gas stream. Adsorbents used to remove acetylene as an impurity therefore have more affinity for acetylene than for other hydrocarbons; such adsorbents capture the acetylene while allowing the product hydrocarbon(s) to pass through the bed. These adsorbents, engineered for trapping acetylene, are not suitable for a process where acetylene is the product gas, and where other relatively small hydrocarbons are impurities requiring removal. To purify acetylene and remove contaminants, an adsorption bed should desirably reject the acetylene and allow it to pass through, while capturing other hydrocarbons.

There remains a need in the art, therefore, for improvements in adsorption technologies for use with commercial acetylene streams, especially to permit the efficient and cost-effective removal of higher acetylene contaminants. These improvements may be particularly advantageous for acetylene streams having relatively low concentrations of higher acetylene contamination, where a product stream of high acetylene purity is desired.

SUMMARY

Disclosed herein, in embodiments, are methods for removing higher acetylenes, such as diacetylene and vinylacetylene, and other higher hydrocarbons, from a gaseous stream comprising a hydrogen fraction and a non-hydrogen fraction, wherein the gaseous stream comprises less than about 4% in total of diacetylene and vinylacetylene, wherein the methods comprise an adsorption step comprising passing the gaseous stream at a preselected superficial linear gas velocity across an adsorption bed supported within an enclosure, the adsorption bed containing a crystalline porous ceramic adsorbent to adsorb the diacetylene and vinylacetylene onto the adsorbent, thereby producing a saturated adsorption bed and a purified gaseous stream comprising less than about 25 ppm of diacetylene and less than about 25 ppm of vinylacetylene; a regeneration step comprising regenerating the saturated adsorbent bed by passing a regeneration gas across the saturated adsorption bed to desorb the diacetylene and vinylacetylene retained thereupon, thereby producing a regenerated adsorbent bed and a contaminated gas stream bearing the diacetylene and the vinylacetylene, and a purging step, comprising removing the contaminated gas stream from the enclosure. In embodiments, the gaseous stream comprises between about 50% and about 90% hydrogen. In embodiments, wherein the non-hydrogen fraction of the gaseous stream comprises greater than about 50% alkynes, or the non-hydrogen fraction of the gaseous stream comprises between about 5% and about 95% acetylene, or between about 10% and 95% acetylene, or between about 20% and about 95% acetylene, or between about 30% and about 90% acetylene, or between about 40% and about 85% acetylene, or between about 80% and about 90% acetylene, or about 85% acetylene. In an embodiment, the gaseous stream comprises less than about 2% of diacetylene, and/or less than about 2% of vinylacetylene. In embodiments, the gaseous stream is directed in a flow direction that is axial to the adsorption bed. In embodiments, the crystalline porous ceramic adsorbent has a surface area greater than 200 $m^2/g$, and pore diameters greater than 0.5 nm; the crystalline porous ceramic adsorbent can be a 13X molecular sieve. In embodiments, the purified gaseous stream comprises less than about 20 ppm of diacetylene, or less than about 10 ppm of diacetylene. In embodiments, the purified gaseous stream comprises less than about 20 ppm of vinylacetylene, or less than about 10 ppm of vinylacetylene. In embodiments, the regeneration gas is heated hot air, and the heated hot air can have a temperature between about 175° C. and about 200° C., or a temperature of about 200° C. or higher. In embodiments, the purging step further comprises exposing the adsorbent bed in the enclosure to a purge gas, and the purge gas is selected from the group consisting of natural gas, hydrogen, nitrogen or purified acetylene. In embodiments, performance of the purge step is followed by subsequent performance of the adsorption step, the regeneration step and the purge step, for a preselected number of performance cycles. In embodiments, the adsorption step is performed in a first enclosing vessel while the regeneration step and the purge step are performed in a second enclosing vessel, with cycling between the adsorption step in one vessel and the regeneration and purge steps in the other vessel for a preselected number of performance cycles. In embodiments, the method further comprises an initial step wherein the gaseous stream is produced by exposing a feed gas comprising a $C_1$-$C_4$ hydrocarbon to an energy source to transform the feed gas into a plasma, wherein the plasma effects conversion of the $C_1$-$C_4$ hydrocarbon into the hydrogen fraction and the non-hydrogen fraction of the gaseous stream. The plasma can be a thermal plasma or a non-thermal plasma. In embodiments, the feed gas comprises methane.

Further disclosed herein, in embodiments, are systems for removing diacetylene and vinylacetylene from a hydrogen-dominant acetylene-hydrogen gaseous stream, wherein the hydrogen-dominant acetylene-hydrogen gaseous stream comprises less than one percent each of diacetylene and vinylacetylene, such a system comprising a first vessel comprising a first adsorbent bed supported in a direction that is transverse to a long axis of the first vessel; a first process gas circuit in fluid communication with the first vessel, comprising a process gas inflow line entering the first vessel through a process gas inlet upstream of the first adsorbent bed for inflow of the hydrogen-dominant acetylene-hydrogen gaseous stream, and further comprising a purified-gas outlet downstream from the first adsorbent bed for outflow of a purified gaseous stream from the first vessel, wherein the hydrogen-dominant acetylene-hydrogen gaseous stream containing diacetylene and vinylacetylene enters the process gas inlet and passes across the first adsorption bed, wherein the diacetylene and vinylacetylene are adsorbed onto the first adsorbent bed to form a first saturated adsorbent bed, and wherein the purified gaseous stream exiting the purified-gas outlet contains less than about 25 ppm each of the diacetylene and vinylacetylene, said first process gas circuit possessing a first set of control valves proximal and distal to the first vessel, the first set of control valves being programmed to permit or prevent flow of process gas through the first process gas circuit; and a first regeneration gas circuit in fluid communication with the first vessel, comprising a regeneration gas line entering the first vessel through a regeneration gas inlet at a first end of the first adsorbent bed for inflow of a regeneration gas, and a regeneration gas outlet exiting the first vessel at a second end of the first adsorbent bed for outflow of a contaminated regeneration gas, wherein the regeneration gas passes across the first saturated adsorption bed from the first end to the second end thereof, and wherein the regeneration gas desorbs the diacetylene and vinylacetylene contaminants from the first saturated adsorption bed in transit across thereof to form the contaminated regeneration gas, said first regeneration gas circuit possessing a second set of control valves, the second set of control valves being programmed to permit or prevent flow of regeneration gas through the first regeneration gas circuit; wherein, when gas is flowing through the first process gas circuit across the first adsorption bed, no gas is flowing through the first regeneration gas circuit across the first adsorption bed, and wherein when gas is flowing through the first regeneration gas circuit across the first adsorption bed, no gas is flowing through the first process gas circuit. In embodiments, the systems further comprise a second vessel identical to the first vessel and having a second adsorption bed; a second process gas circuit identical to the first process gas circuit and in fluid communication with the first process gas circuit and the second vessel; and a second regeneration gas circuit identical to the first regeneration gas circuit and in fluid communication with the first regeneration gas circuit and the second vessel, wherein, when gas is flowing through the first process gas circuit across the first adsorption bed in the first vessel, regeneration gas is flowing through the second regeneration gas circuit across the second adsorption bed in the second vessel. In embodiments, when gas is flowing through the second process gas circuit across the second adsorption bed in the second vessel, regeneration gas is flowing through the first regeneration gas circuit across the first adsorption bed in the first vessel. In embodiments, gas flow through the first process gas circuit across the first adsorption bed runs countercurrent to gas flow through the first regeneration gas circuit across the first adsorption bed.

Figure 1:
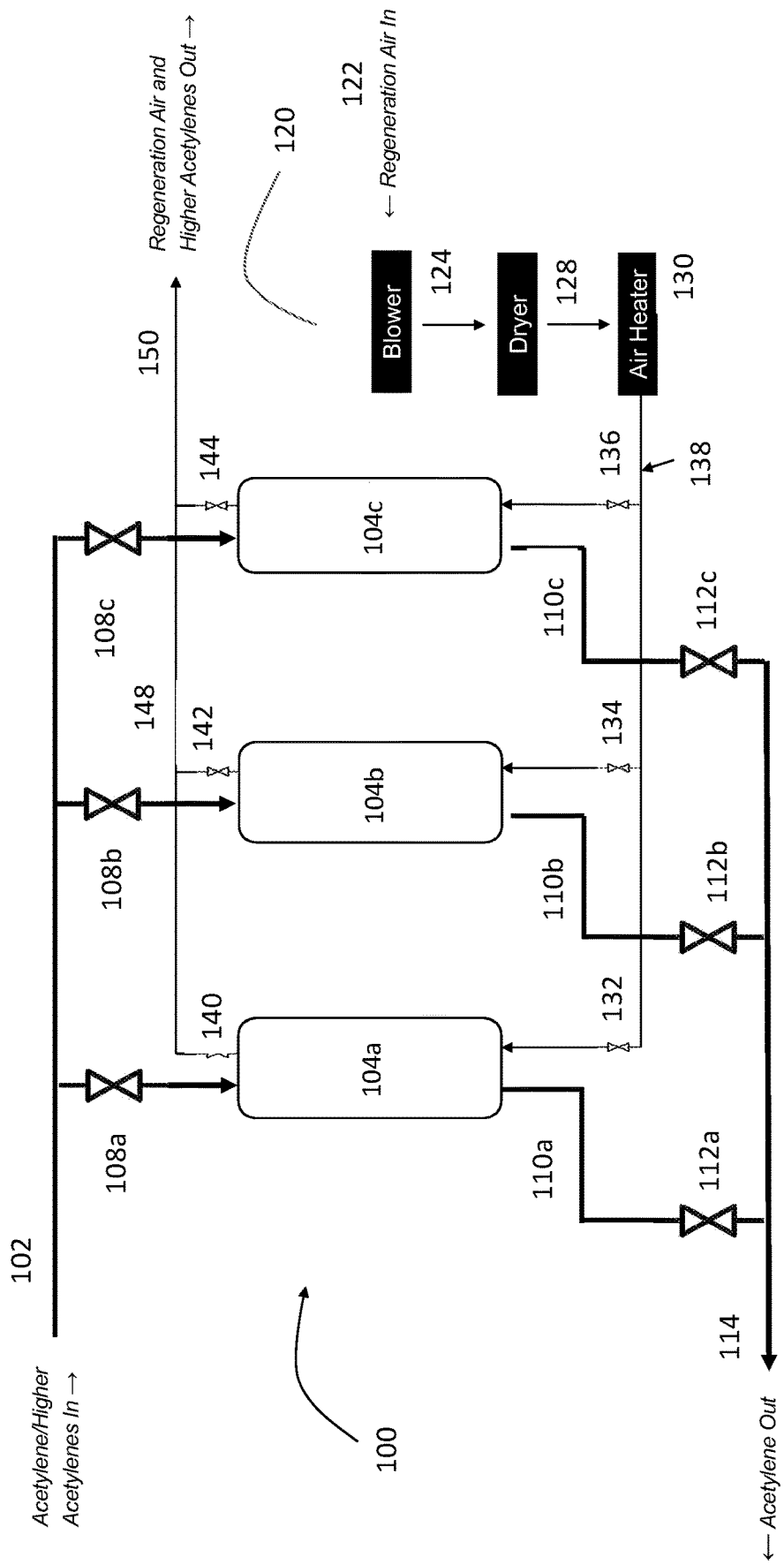
FIG. 1 depicts schematically a purification/separation system suitable for acetylene purification.

DETAILED DESCRIPTION a. Systems and Methods in General

Disclosed herein, in embodiments, are highly selective systems and methods for removing higher acetylenes, including, but not limited to, diacetylene and vinylacetylene, from gaseous streams comprising acetylene gas. These systems and methods are particularly suitable for gaseous streams that only contain minimal amounts of hydrocarbon contaminants, for example, a hydrogen-dominant acetylene-hydrogen gaseous stream in which the acetylene fraction is between about 5% and about 25% vol/mol % of the overall composition of the feed gas. In such a hydrogen-dominant acetylene-hydrogen gaseous stream, the hydrogen fraction can range from about 60% to about 90%, depending on the amount of acetylene present, and depending on the presence of other components, for example, methane.

In such a stream, the higher acetylenes can be present in amounts of less than about 5% (vol/mol %) of the overall composition of the feed gas, for example, having vinylacetylene and diacetylene present in total at less than about 4.5% of the overall composition of the feed gas, or having vinylacetylene and diacetylene present in total at less than about 4% of the overall composition of the feed gas, or having vinylacetylene and/or diacetylene present in amounts of less than about 2%. In an embodiment, the higher acetylenes can be present in amounts of less than about 4% (vol/mol %) of the overall composition of the feed gas, for example, having vinylactylene and diacetylene present in total at less than about 3.5%, or less than about 3% of the overall composition of the feed gas, or having vinylacetylene and/or diacetylene present in amounts of less than about 1.75% or about 1.5%. In an embodiment, the higher acetylenes can be present in amounts of less than about 2.5% (vol/mol %) of the overall composition of the feed gas, for example, having vinylacetylene and diacetylene present in total at less than about 2% of the overall composition of the feed gas, or having vinylacetylene and/or diacetylene present in amounts of less than about 1%. In various embodiments, other higher order hydrocarbons can be present in amounts of less than about 0.3%, 0.2% or 0.1 percent, with vinylacetylene and diacetylene present in total at less than about 2%, or less than about 3%, or less than about 3.5%, or less than about 4% of the overall composition of the feed gas.

As a result of the purification/separation processes disclosed herein, the amounts of higher acetylenes can be reduced to amounts less than 25 ppm each in such gaseous streams, or can be reduced to amounts less than 20 ppm each in gaseous streams or can be reduced to amounts less than 15 ppm each in such gaseous streams. In embodiments, the amounts of diacetylene and vinylacetylene can be reduced to amounts less than about 25 ppm each in such gaseous streams, or to amounts less than about 20 ppm each in such gaseous streams, or to amounts less than 15 ppm each in such gaseous streams, or to amounts less than about 10 ppm each in such gaseous streams. In other embodiments, there may be different amounts of diacetylene and vinylacetylene in the gaseous stream, but with each amount present in an amount of less than 25 ppm.

In embodiments, the purification/separation system disclosed herein comprises a temperature-swing adsorber to be used in conjunction with a reactor capable of producing a hydrogen-dominant feed gas stream with acetylene as the primary hydrocarbon product. Such a gaseous stream can be produced by exposing a hydrocarbon gas, for example, methane, ethane, propane, or butane, to energy in the reactor that creates a non-thermal plasma, thereby generating hydrogen gas as well as the major product acetylene plus a range of minor hydrocarbon components. The purification/separation methods described herein can then be employed to remove the impurities from the gas stream emerging from the reactor, so that substantially pure acetylene is formed in the product stream.

In an embodiment, the system for purification/separation comprises a series of at least two vessels containing an adsorbent, where the adsorbent is non-selective to the acetylene molecules while retaining the higher acetylene molecules. As used herein, the term "adsorbent" refers to a porous material having a high surface area allowing for a high capacity of adsorbate. Each vessel is in fluid communication with the feed gas fluid stream so that its adsorbent can adsorb the contaminants of interest from the feed gas as it passes over the adsorbent, i.e., the higher acetylene molecules. In an embodiment, the adsorbent in each vessel is regenerated via an inflow stream of heated gas that can dislodge and remove the adsorbate from the adsorbent, thereby preparing the adsorbent for further exposure to the feed gas and its contaminants. In other embodiments, the adsorbent itself can be heated to regenerate it, thereby dislodging the adsorbate from the adsorbent and preparing the adsorbent for further exposure to the feed gas. Combinations of internal and external heating techniques can also be used to effect adsorbent regeneration. The cycles of adsorption and desorption in each vessel are coordinated with those in the other vessel or vessels to optimize the efficiency of contaminant removal and adsorption regeneration. Advantageously, multiple sets of valves can be programmed to coordinate the inflow and egress of the acetylene-bearing gas stream, and the inflow and egress of the regeneration stream.

Disclosed herein in embodiments are systems and methods for separating alkyne $C_2$ molecules (e.g., acetylene) from higher acetylenes, including, but not limited to, alkyne $C_4$ molecules, by tuning time-on-stream for an adsorption system based on gas flow rate, gas composition, adsorbent capacity, and adsorbent amount. This is especially advantageous for alkyne $C_4$ molecules. Surprisingly, the time-on-stream for separating alkyne $C_2$ molecules from alkyne Cos does not follow the trend seen in separating other pairs of hydrocarbons that are close to each other in size, for example, separating alkane $C_{1S}$ from alkane $C_{3S}$, or alkane $C_{2S}$ from alkane $C_{4S}$, or olefin $C_{4S}$ from olefin $C_{6S}$. It has been discovered that an adsorption system can be constructed to provide a sufficient adsorption time window for industrially feasible separation of alkyne $C_4$ molecules from acetylene. The following equation can provide a guide for identifying a desirable time on stream for this separation:

$$\text{Time on Stream} = \frac{22.4 \text{ (adsorbent capacity)(adsorbent mass)}}{\text{(impurity concentration)(total flow rate)}} \quad \text{EQ. 1}$$
$$\text{(molar mass of impurity)}$$

When the adsorbent bed is fresh, all components of the gas are adsorbed. The adsorbate is in constant equilibrium between binding on and releasing off the surface of the adsorbent. As the majority of the surface of the adsorbent becomes covered in adsorbate, a period of competition begins between the various gas components in the stream. Those components with more of a propensity to bind (for example, to condense (lower vapor pressure)) and/or with a stronger attraction to the adsorbent will occupy more sites on the adsorbent for longer periods of time, causing displacement of the molecules with weaker attraction or higher vapor pressures. For purposes of these systems and methods, it is known that higher acetylenes have a greater attraction to certain adsorbents and a lower vapor pressure than acetylene. This leads to the contaminant molecules displacing acetylene molecules off the surface of the adsorbent. In such a way, the separations of higher acetylenes from acetylene can be accomplished with very little acetylene loss, leading to a very selective removal process.

b. System Exemplification

An exemplary embodiment of a purification/separation system for removal of higher acetylenes from an acetylene stream is depicted in FIG. 1. As shown in FIG. 1, a purification/separation system can comprise an adsorption subsystem 100 and an adsorber regeneration subsystem 120. The adsorption subsystem includes a plurality of adsorbent-containing vessels 104a, 104b, and 104c. In the depicted embodiment, three adsorbent-containing vessels are shown, but other vessel arrangements are also effective having different numbers of vessels, or even a single vessel in which adsorption alternates with desorption. A gaseous stream 102 containing acetylene and the higher acetylene contaminants is directed into each adsorbent-containing vessel 104a, 104b, and 104c through a dedicated inlet valve for that vessel 108a, 108b, and 108c. The gaseous stream 102 optionally has been purified before being routed into the adsorption subsystem 100 by removing solids and heavier hydrocarbons from the gaseous stream, and it has furthermore been cooled, for example to a temperature between 35-40° C.; mechanisms for the preliminary preparation of the gaseous stream 102 are not shown in FIG. 1.

The adsorber vessels shown in FIG. 1 can be deployed in a 2+1 configuration, meaning that while two of the adsorber vessels are active in adsorbing the higher acetylenes from the gaseous stream 102, one of the vessels is in a regeneration mode, wherein the adsorbent is being regenerated by exposure to a regeneration air flow being provided through the regeneration subsystem 120. For example, the gaseous stream 102 can be directed into vessels 104a and 104b through their inlet valves 108a and 108b, while the inlet valve 108c is closed, preventing entry into vessel 104c while it is being regenerated. In an embodiment, is desirable to split the gaseous stream 102 inflow evenly between the two active adsorption vessels. In other embodiments, the active adsorption vessels may be at different stages of adsorption, with the timing of valve opening scheduled so that one active vessel completes its adsorption sequence and enters the regeneration mode before the other.

After exposure to the adsorbent in the working adsorbent vessel, the gaseous stream exits the vessel through its respective exit line 110a, 110b, and 110c, passing through an outflow valve 112a, 112b, and 112c, to enter an outflow line 114. The outflow line contains acetylene from which vinylacetylene and diacetylene have been removed, those molecules having been adsorbed by the adsorbent within the adsorption vessels. When the adsorbent in each adsorption vessel is saturated with the removed species, it is regenerated by exposure to a regeneration gas 138 that is provided from the regeneration circuit 120.

In one embodiment, the amount of adsorbent placed in each vessel 104a, 104b, 104c is selected such that each vessel can adsorb for 16 hours and regenerate for 8 hours, as described below. Thus each vessel 104a, 104b, 104c can turn over a full cycle every 24 hours. The sequencing for an exemplary system 100 is shown in Table 1, where the adsorption periods are staggered in 8-hour segments, allowing for continuous operation.

TABLE 1

| Vessel A | Online | Online | Regenerating |
|---|---|---|---|
| Vessel B | Online | Regenerating | Online |
| Vessel C | Regenerating | Online | Online |
| Time on Stream (hours) | 8 | 16 | 24 |

As exemplified in FIG. 1, a vessel 104c can receive an inflow gaseous stream 102 for 8 hours by opening valves 108c and 110c, while another vessel 102b is simultaneously taken offline by closing valves 108b and 112 b. Regeneration can be commenced in vessel 102b by opening up regeneration stream valves 134 and 142, allowing the regeneration gas 138 to heat the entire vessel 102b. In some embodiments, the maximum regeneration temperature is held for 2 hours while the hot air is flowed at 33% of the acetylene process mass flow rate. Afterwards, the heating is ceased, and the air flow is continued until the vessel reaches room temperature. Following the regeneration of the adsorbent in vessel 102b, the contaminant-bearing regeneration gas 148 exits the vessel 102b and the valves 134 and 142 are closed. Following adsorbent regeneration, the vessel 102b can be purged of the regeneration gas via vacuum or via exposure to a purge gas (not shown) to prevent subsequent contamination of the freshly introduced acetylene-containing feed gas that is to be adsorbed the next cycle. In embodiments, purge gas can be natural gas, hydrogen, nitrogen or purified acetylene; in other embodiments, the vessel containing the freshly regenerated adsorbent is evacuated and presaturated with scrubbed process gas from the other two vessels. Following satisfactory purging, the vessel 104b can then be refilled and/or repressurized by allowing a backflow of scrubbed acetylene from the outflow line 113, by opening valve 112b and closing valve 142. The vessel 104b is then ready to come online by opening valve 108b, thereby one again exposing the adsorbent in the vessel 104b to contaminant-bearing gaseous stream 102.

In more detail, regeneration is carried out by passing a regeneration gas 138 into each vessel after its adsorbent has become saturated with higher acetylene species to be removed. The regeneration gas 138 can be produced by conditioning a gas stream, such as ambient air, to heat it and dry it. As shown in FIG. 1, a stream of regeneration air 122 passes through a blower 124, and is then dehumidified with a desiccant 128 and heated by an air heater 130. Thus treated, the conditioned regeneration gas 138 enters the adsorbent vessels 104a, 104b, 104c through air inflow valves 132, 134, 136, to pass through such vessels and regenerate the adsorbent, as described above. The regeneration air removes the higher acetylenes from the surfaces of the adsorbent to exit each adsorption vessel through the exit valves 140, 142. 144. The timing of entry and exit of the regeneration gas is arranged in relation to the purification process; adsorbent regeneration takes place when the adsorbent vessel offline from the purification process. After removing the higher acetylenes from the adsorbent, the contaminant-bearing regeneration gas 148 exits the system through an outflow path 150, for disposal, flaring, or further processing.

In an embodiment, regeneration can be performed using hot air at a temperature greater than 200° C., for example 250° C. In this embodiment, ambient humid air is the regeneration air 122, which is forced into the system using a ring blower 124. The forced hot air then then passes through a desiccant 128. In embodiments the desiccant can be single use or regeneratable, such a continuous flow rotary desiccant. Drying the regeneration air 122 is especially important when certain materials are used as desiccants in the adsorption vessels 104a, 104b, 104c. For example, hot water or steam can decrease adsorbent capacity, and can degrade certain zeolite-based adsorbents such as a 13X molecular sieve. After being dried, the regeneration air can then be heated in an air heater 130, such as an inline ceramic element heater, an inline duct heater using wire loops, or an inductive heater. The hot, dry air then passes upwards into a vessel across the adsorbent being regenerated, for example vessel 104b, via an open valve 134. The regeneration air desorbs the higher acetylenes when it passes over the saturated adsorbent, and then exits the vessel 102b and the system as described above. In the depicted embodiment, the flow direction for the regeneration gas can be countercurrent to the process flow, although in other embodiments, the flow direction for the regeneration gas can be the same as the flow direction for the process flow, so long as the regeneration gas is not flowing through the adsorbent at the same time as the process flow.

A purification/separation system as described herein is advantageous for removing higher acetylenes, such as vinylacetylene and diacetylene, from mixed acetylene/hydrogen streams, such as may be produced from a nonthermal plasma reactor that uses $C_1$-$C_4$ hydrocarbons as feed gases. A non-limiting example of such a plasma reactor is described in U.S. Published Pat. App. No. 20200063040, the contents of which are expressly incorporated by reference herein. Using methane as a feed gas, such a reactor breaks the C—H bonds with resultant formation of hydrocarbon radicals $CH_3^*$, $CH_2^*$, $CH^*$, along with $H^*$, and C. These radicals can recombine to form two-carbon fragments as exemplified by the following equations:

$$CH_3^* + CH_3^* \rightarrow C_2H_6$$

$$CH_2^* + CH_2^* \rightarrow C_2H_4$$

$$CH^* + CH^* \rightarrow C_2H_2$$

$$CH_3^* + CH^* \rightarrow C_2H_4$$

$$CH_3^* + CH_2^* \rightarrow C_2H_4 + H^*$$

$$CH_3^* + CH^* \rightarrow C_2H_4$$

$$CH_3^* + CH^* \rightarrow C_2H_2 + H_z$$

$$CH_2^* + CH^* \rightarrow C_2H_2 + H^*$$

In addition, methane can combine with various radicals to form two-carbon fragments as exemplified by the following equations:

$$CH_4 + CH_3^* \rightarrow C_2H_6 + H^*$$

$$CH_4 + CH_2^* \rightarrow C_2H_6$$

$$CH_4 + CH_2^* \rightarrow C_2H_4 + 2H/H_2 CH_4 + CH^* \rightarrow C_2H_4$$

$$CH_4 + CH^* \rightarrow C_2H_2 + H^* + H_2$$

Besides the illustrated reactions to form two-carbon fragments, higher-order hydrocarbons, for example higher acetylenes, can be formed by appropriate recombinations of plasma-generated radicals with each other and with the precursor gas. As described above, these higher acetylenes such as vinylacetylene and diacetylene are advantageously removed from the acetylene stream using the systems and methods disclosed herein.

As described above, the systems and methods of removing higher acetylene byproducts, such as diacetylene and vinylacetylene, can be used to process an acetylene-comprising stream produced by the plasma reactor described in U.S. Published Pat. App. No. 20200063040, the contents of which are expressly incorporated by reference herein. In certain specific embodiments, the invention encompasses a gas processing system for transforming a hydrocarbon-containing inflow gas into outflow gas products comprising acetylene and hydrogen, wherein the system comprises a gas delivery subsystem, a plasma reaction chamber, a microwave subsystem, and a subsystem for removing higher acetylenes, such as diacetylene and vinylacetylene, from a stream comprising the outflow gas products as described herein, wherein the gas delivery subsystem is in fluid communication with the plasma reaction chamber and directs the hydrocarbon-containing inflow gas into the plasma reaction chamber, wherein the microwave subsystem directs microwave energy into the plasma reaction chamber to energize the hydrocarbon-containing inflow gas thereby forming a plasma in the plasma reaction chamber, wherein the plasma effects the transformation of a hydrocarbon in the hydrocarbon-containing inflow gas into the outflow gas products that comprise acetylene and hydrogen. In yet additional aspects, the invention includes a method of processing a hydrocarbon-containing inflow gas to produce acetylene gas, comprising providing the hydrocarbon-containing inflow gas, injecting the hydrocarbon-containing inflow gas into a plasma reaction chamber, energizing the hydrocarbon-containing inflow gas in the reaction chamber with microwave energy to create a plasma; forming outflow gas products in the plasma, wherein one of the gas products is the acetylene gas; flowing the outflow gas products to exit the reaction chamber, and removing the higher acetylenes such as diacetylene and vinylacetylene from the outflow gas products using the methods described herein. In certain specific aspects, the plasma is a non-thermal plasma. In additional aspects, the system and method further comprising vacuum subsystem; for example, the vacuum subsystem maintains a reduced pressure environment for the outflow gas products. The reduced pressure environment can, for example, be a pressure between about 30 to about 120 Torr.

As an example of purification/separation effectiveness using the systems and methods described herein, the following Table 2 lists the pre-treatment and the post-treatment levels of various components in the feed gas and product gas streams, where the feed gas is a gaseous fluid stream produced by a nonthermal plasma using methane as a precursor gas, and where the feed gas enters a purification/separation system such as is illustrated in FIG. 1, with a product gas exiting the purification/separation system.

TABLE 2

| Gas | Feed Gas Component (%) | Product Gas Component (%) |
|---|---|---|
| hydrogen | 84.6 | 85.3 |
| acetylene | 12.8 | 12.9 |
| methane | 1.27 | 1.28 |
| nitrogen | 0.43 | 0.43 |
| carbon dioxide | 0.11 | 0.11 |
| methylacetylene | 0.01 | 0.01 |
| diacetylene | 0.41 | <10 ppm |
| vinylacetylene | 0.09 | <10 ppm |
| benzene | 0.01 | <10 ppm |

Adsorption vessels for the adsorption subsystem 100 can be arranged in series or in parallel. In embodiments, it is desirable that each adsorption vessel be similar to the others in its specifications so that the vessels may be used interchangeably for adsorption and regeneration, in accordance with a predetermined sequence. Timing and sequencing of adsorption and desorption among the system vessels can be calibrated based on vessel configurations, gaseous inflow patterns, adsorbent choice, and other variables familiar to skilled artisans. For example, a vessel configuration and adsorption/desorption sequencing can be chosen based on variables such as flow rate (high flow rates, for example, can cause pressure drop across the adsorbent, so that the flow may need to be split across multiple vessels), adsorbent sensitivity, regeneration time, and the like. Simple systems can be arranged with only two tanks that then alternate between adsorption and regeneration. Multi-vessel systems are more expensive initially, with the requisite piping and electronics and component costs, but may be cost-effective in high flow situations.

With a three-vessel purification/separation system, a 2+1 sequencing can be employed, with two vessels online at one time while one vessel regenerates. In other embodiments 1+2 sequencing can be employed, with one vessel online while two vessels are regenerating. In an embodiment, a 2+1 staggered system can be used, where the two vessels that are online at the same time are staggered in their online status by 8 hours, so that they do not become saturated at the same time.

An exemplary scheme of duty cycles is shown in Table 3 below. This sequencing arrangement assumes that the adsorption bed retains its efficacy for 16 hours and regenerates adequately over 8 hours. In this arrangement, the regeneration of the three beds is staggered so that they regenerate consecutively in a single day.

TABLE 3

| Hour | 0 | 8 | 16 | 24 |
|---|---|---|---|---|
| Vessel 1 | On | On | Regen | On |
| Vessel 2 | On | Regen | On | On |
| Vessel 3 | Regen | On | On | Regen | c. System Components

Figure 2:
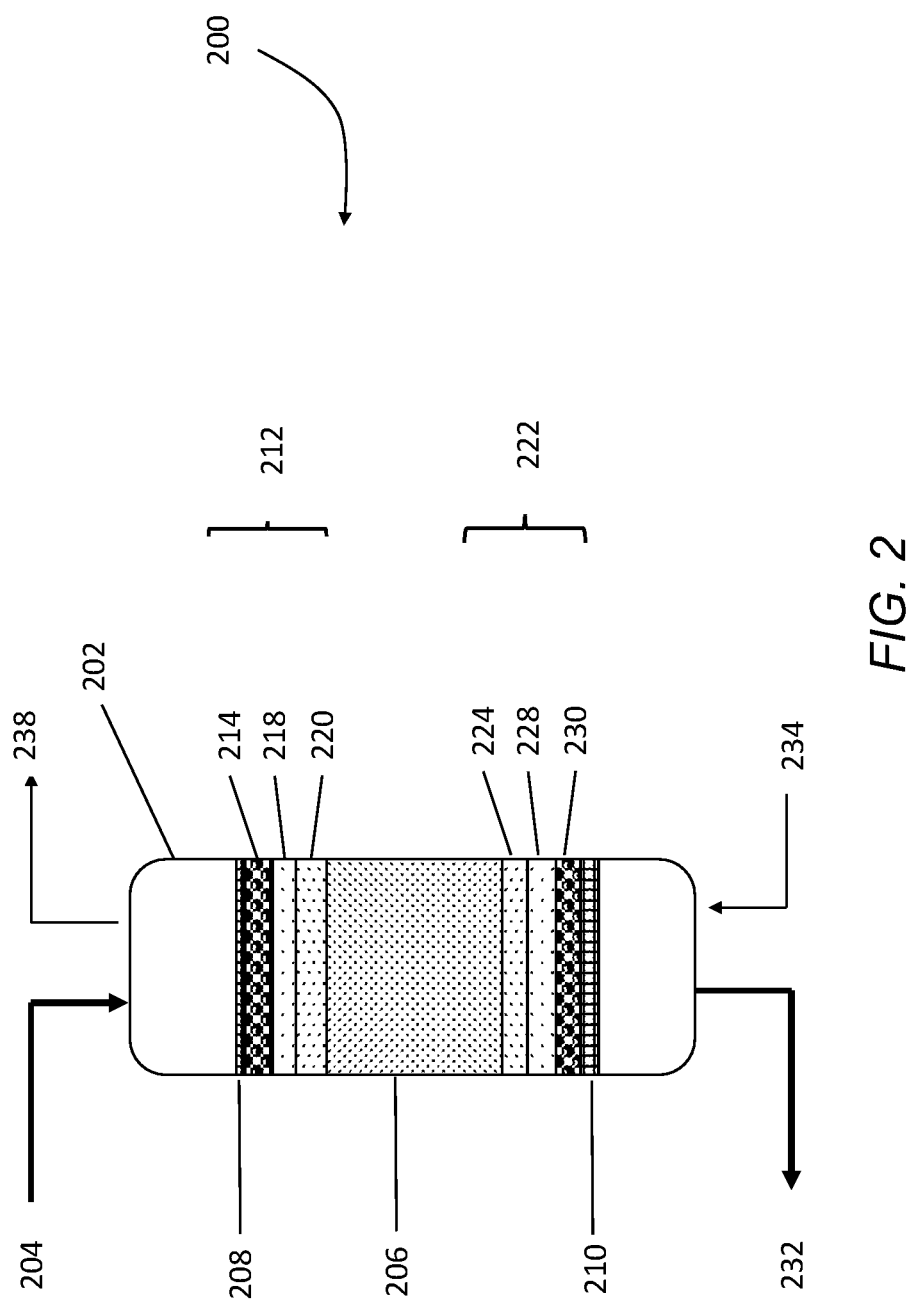
FIG. 2 depicts an embodiment of an adsorbent vessel.

An embodiment of an adsorbent-containing vessel suitable for use with the systems and methods disclosed herein is illustrated in FIG. 2. As shown in FIG. 2, an adsorbent system 200 comprises an adsorber vessel 202 and an adsorbent material 206 disposed therein. The adsorber vessel 202 is in fluid communication with a gaseous inflow tract 204 through which a feed gas enters the adsorber vessel 202, and in fluid communication with a product outflow tract 232 through which the product gas (i.e., the feed gas stripped of selected contaminants) exits the adsorber vessel 202. The adsorber vessel 202 is also in fluid communication with an air inflow tract 234 through which regeneration air enters the adsorber vessel 202, and in fluid communication with an air outflow tract 238 through which the contaminated regeneration air (i.e., the regeneration air bearing the selected contaminants) exits the adsorber vessel 202. In the depicted embodiment, the direction of flow for the feed gas through the adsorber vessel 202 is opposite the direction of the regeneration air through the adsorber vessel 202, although in other embodiments, the direction of flow for the feed gas can be the same as the direction of flow for the regeneration air. In either case, the flow of the two gaseous streams (feed gas and regeneration air) are synchronized so that they are not both flowing at the same time: in other words, the feed gas is not passing through the adsorbent at the same time as the regeneration air.

In the depicted embodiment, the adsorbent material 206 is sandwiched between an upper diffuser 212 and a lower diffuser 222. The upper diffuser 212 can include three layers of diffuser particles, an upper layer 214, a middle layer 218, and a lower layer 220. Similarly, the lower diffuser 222 can include three layers of diffuser particles, an upper layer 224, a middle layer 228, and a lower layer 230. The lower diffuser 222 is supported by a support mesh 210 disposed below the lower layer 230 of diffuser particles. The upper diffuser 212 is contained superiorly by a retention mesh 208 placed on top of the upper layer 214 of diffuser particles.

For adsorption of higher acetylenes from a hydrocarbon stream where acetylene is the predominant hydrocarbon and contaminant levels are low, an adsorbent 206 can be selected with a high surface area (e.g., >300 m$^2$/g) to allow for high capacity of adsorbate. Advantageously, the average diameter of the adsorbent's pores should be large enough to allow diffusion of the largest molecules contained in the feed gas. In embodiments, the largest molecules in a hydrocarbon stream where acetylene is the predominant hydrocarbon can be aromatic hydrocarbons, containing for example 6-8 carbons. In such an embodiment, an adsorbent 206 can be selected having a pore size greater than 0.6 nm, so that the feed gas can diffuse into the pores of the adsorbent material 206 and pass over the majority of the adsorbent's surface area. Adsorbent materials 206 can be organic (e.g., activated carbon) or inorganic (e.g., diatomaceous earth, zeolites, silica, zirconia, ceria, alumina, or other ceramics).

In one embodiment, a molecular sieve can be used. Molecular sieves are materials whose atoms are configured in a latticework that supports a large number of interconnected, uniformly sized pores. These pores allow for the passage of molecules that are of a size equal to or smaller than the pores. Molecular sieves, therefore, allow segregation of molecules according to size. One class of molecular sieve is formed from zeolites. Zeolites are hydrated aluminum silicates, frequently containing exchangeable cations. Zeolites can be naturally occurring or artificial. Naturally occurring zeolites include materials such chabazite, clinoptilolite, erionite, heulandite, mordenite, and the like. Artificial zeolites include, inter alia, types A, D, L, R, S, T, X, Y, ZSM, and the like, with their nomenclature typically including a numerical designation or the abbreviation of the predominant cation.

In embodiments, a 13X molecular sieve, which has pore diameters of approximately 0.9 nm, is suitable for the adsorbent material 206. The particles of adsorbent material 206 should be sized to prevent significant amounts of pressure drop across the bed (i.e., a pressure drop of less than 10 psi); therefore, powders are not appropriate for almost all but the smallest scale adsorption systems. In an embodiment, the adsorbent particle size is 1/16 inch (1-2 mm) spheres of molecular sieve 13X. In other embodiments, the adsorbent can be pellet- or rod-shaped. For use in systems with very large process flow rates, the adsorbent material 206 can be arranged in layers, for example, a 1/16 inch molecular sieve layered with 1/8 inch molecular sieve to decrease pressure drop.

As depicted in FIG. 2, and in more detail, the adsorbent material 206 can be disposed between an upper diffuser 212 and a lower diffuser 222, which structures are intended to further diffuse the inflow gas (whether feed gas or regeneration gas) before it encounters the adsorbent material 206. As depicted, the upper diffuser 212 and lower diffuser 222 each includes an upper, middle, and lower layer. Each layer contains a homogenously-sized arrangement of diffusion particles; the particle size in each layer differs from the particle size in the other adjacent layers. Ceramic particles, such as Denstones® support media (St-Gobain NorPro), are particularly advantageous for use in the upper diffuser 212 and the lower diffuser 222. Ceramic particles such as these provide a tortuous path to facilitate gas diffusion. Moreover, ceramic particles provide weight to hold the adsorbent in place as a gas stream flows through it. This is particularly useful during regeneration, when the flow is directed upward through the adsorbent bed. If the adsorbent material 206 is not held down by weight or is not otherwise confined, its repetitive floating and settling during consecutive cycles can cause attrition and a decrease in its useful life.

Particle size for the three layers (upper, middle, lower) of the upper diffuser 212 and the lower diffuser 222 can be selected so that the particle size between two contiguous layers varies by about a factor of two. For example, ceramic spheres in the upper layer of the upper diffuser can have a diameter of ½", while the ceramic spheres of the middle layer can have a diameter of about ¼", and the ceramic spheres of the lower layer can have a diameter of about 1/8". The upper, middle, and lower layers of the lower diffuser can be similarly sized: for example the ceramic spheres of the upper layer can have a diameter of 1/8", while the ceramic spheres of the middle layer can have a diameter of about ¼", and the ceramic spheres of the lower layer can have a diameter of about ½". This rule of thumb prevents migration of one layer into another, which can cause irregularities in the diffuser or the adsorber material 206 that can lead to channeling and early breakthrough of the contaminants. In embodiments, the insulating ceramic particles can be replaced with conducting material such as aluminum for those applications that require faster cooling cycles.

In embodiments, the adsorption vessel 202 is designed so that the superficial linear velocity of the feed gas is kept below a certain value, for example, less than about 500 cm/min, or less than about 1000 cm/min, or less than about 1500 cm/min, or less than about 2000 cm/min. When the superficial linear velocity of the gas exceeds this metric, adsorption efficiencies begin to drop, and the effective capacity of the adsorbent is decreased. Since most feed gas flow rates are fixed, this is generally accomplished by maintaining a minimum vessel diameter. However, an adsorption vessel 202 typically has a maximum vessel diameter, following the general rule of thumb, L/D>2, where L is the height of the vessel and D is the diameter. When vessel diameters exceed this metric, heat transfer to the walls of the vessel becomes less efficient and the vessel becomes more expensive.

In an embodiment, as the feed gas enters the adsorption vessel 202, it is directed radially towards the walls of the vessel 202 using an inlet flow diffuser (not shown), thus producing even flow distribution across the adsorbent perpendicularly to the flow direction. Uneven flow distribution can prevent the feed gas from coming in contact with all the adsorbent, resulting in early breakthrough of contaminants into the product stream. In addition to or in place of an internal mechanism such as an inlet flow distributer or gas diffusion plates, a minimum distance can be maintained between the inlet of the vessel and the upper aspect of the upper diffuser system, for example the retention mesh 208. The minimum distance is selected to allow enough time for the feed gas to spread out radially towards the walls of the vessel before it comes in contact with the retention mesh and the diffusion structures below it.

Advantageously, the feed gas stream passes in an axial direction through the adsorber vessel 202, flowing from the gaseous inflow tract 204 to the product outflow tract 232. The feed gas stream can travel across the adsorbent material 206 at a superficial gas velocity of less than about 500 cm/min, or less than about 1000 cm/min, or less than about 1500 cm/min, or less than about 2000 cm/min. In embodiments, the adsorbent material 206 can have a surface area that is greater than about 200 m$^2$/g, with pore diameters greater than 0.5 nm. Advantageously, adsorption takes place over two hours or longer.

Advantageously, the adsorption process takes place at low temperatures, for example, less than 100° C., while the adsorbent is regenerated with hot gas at temperatures above 150° C., or above 175° C., or between 175° C. and about 200° C., or above about 200° C., with optional cooling after adsorbent regeneration.

Advantageously, the maximum regeneration temperature is held constant for 2 hours while the hot air is flowed at a rate greater than 33% of the mass flow rate for the feed gas, for example at a rate between about 33% and about 500% of the mass flow rate. In an embodiment, the maximum regeneration temperature is held constant for 2 hours while the hot air is flowed at 100% of the feed gas mass flow rate.

While the adsorber system depicted in FIG. 2 has demonstrated particular advantages for the systems and methods disclosed herein, other suitable structures for adsorber vessels can be envisioned. For example, the bottom support mesh 210 can be replaced with another support mechanism, for example a perforated plate, or can be eliminated entirely. Other structural variations can be readily envisioned by artisans of ordinary skill without departing from the spirit and scope of the invention as disclosed herein.

Figure 3:
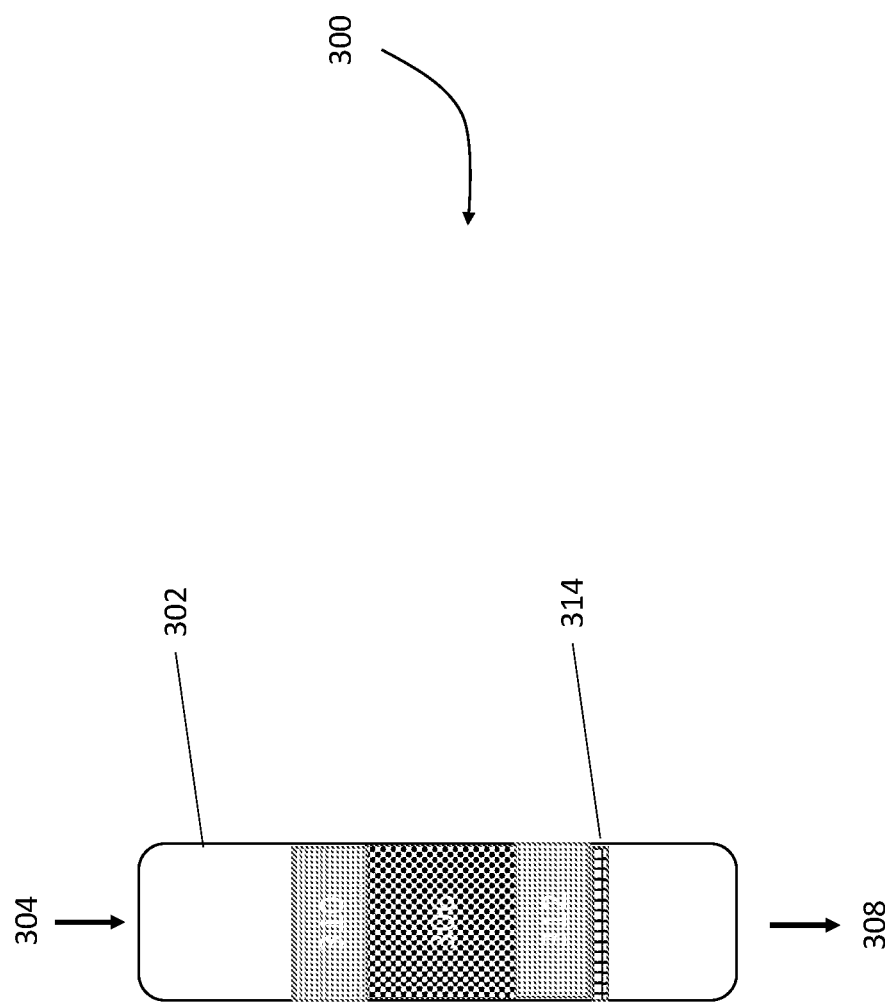
FIG. 3 depicts an embodiment of an adsorbent vessel.

For further illustration of a more general system that can be customized as needed, an adsorber system 300 is depicted in FIG. 3, showing generally the adsorption vessel 302 and its contents, but not showing a mechanism for adsorbent regeneration. As shown in FIG. 3, an adsorbent system 300 comprises an adsorber vessel 302 having an inflow tract 304 and an outflow tract 308 and containing an adsorbent material 306. A gaseous stream containing a desired product gas and a variety of contaminants (i.e., a feed gas) enters the adsorber vessel 302 through the inflow tract 304, passes through the adsorbent material 306, and exits the adsorber vessel 302 via the outflow tract 308. The adsorbent material 306 can be any adsorbent material that is suitable for removing the contaminants from the feed gas, for example a molecular sieve as described above. The gaseous stream exits the adsorber vessel 302 having been separated from its contaminants, which have been adsorbed by the adsorbent material 306 within the vessel 302. The adsorbent material 306 is supported by a lower packing material 312 that rests on a support flooring 314. The positioning of the adsorbent material 306 is reinforced by an upper packing material 310 that retains the adsorbent material 306 superiorly. In an embodiment, the adsorber vessel 302 can have a height of about 8 feet, with the adsorbent material 306 having a bed height of two feet. The upper and lower packing materials have a bed height of about one foot. The distance from the support flooring 314 to the outflow tract 308 is about two feet. Other dimensions can be substituted for these illustrative ones, as would be understood by those of ordinary skill in the art.

d. System Variations

Figure 4B:
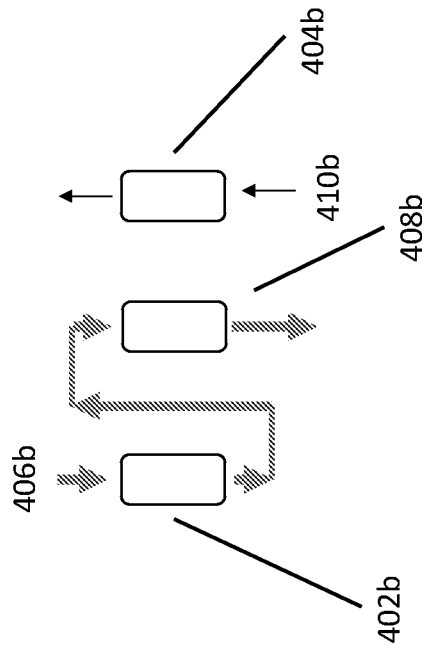
FIGS. 4A and 4B depict schematically purification/separation systems suitable for acetylene purification.
Figure 4A:
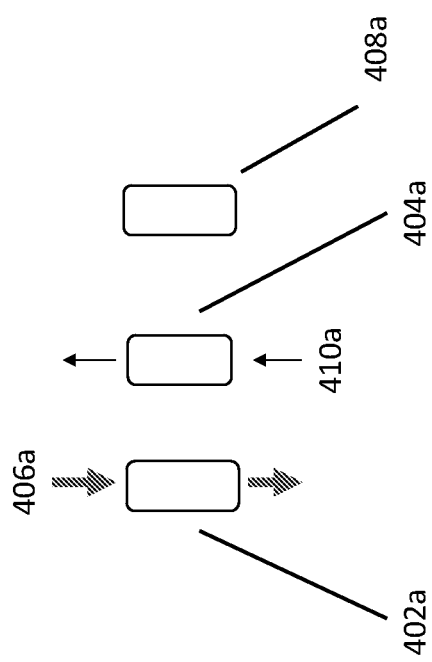

While certain embodiments of purification/separation system for removal of higher acetylenes from an acetylene stream have been described above using three tanks with alternating adsorption and regeneration schemes, other embodiments can be envisioned. For example, as shown in FIG. 4A, two tanks can be used with adsorption being carried out in one tank 402a while regeneration is carried out in the other 404b; in the depicted embodiment, the adsorption tank 402a is exposed to the gaseous stream 406a containing the gas to be treated, and the regeneration tank 404b is exposed to the regeneration gas stream 410a. In the depicted embodiment, the adsorption period in the adsorption tank 402a is the same as the regeneration period in the other tank 404b, for example, 8 hours. At the conclusion of this 8-hour period, the gas flows are reversed, so that the adsorption tank 402a is regenerated with the regeneration gas stream and the and the regeneration tank 404a is exposed to the gaseous stream containing the gas to be treated, and performs the adsorption of its impurities. In the depicted embodiment, an optional spare tank 408a is offline. In an alternative example, as shown in FIG. 4B, an adsorbent system arrangement can employ one tank as the adsorbent tank 402b, one tank as the regeneration tank 404b, and one tank as a guard bed 408b. The path 406b of the gaseous stream containing the gas to be treated passes from the adsorbent tank 402b into the guard bed 408b, while the flow path 410b for the regeneration gas passes through the regeneration tank 404b. The guard bed 408b acts as a redundant bed downstream of the active adsorbing bed 402b. The guard bed 408b, in series with the adsorbing bed 402b, provides an extra measure of safety, so that if there is a minor amount of contaminant that is not removed in the adsorbing bed 402b, it would be removed by exposure to the adsorbent in the guard bed 408b. This configuration is advantageous for those cases where a very high purity of acetylene product is required; as a downside, the configuration is more expensive and can require more pressure management at larger scales to avoid undesirable pressure drops across the two beds. Thus, this configuration may be more suitable for lower flow situations and smaller systems.

Table 4 presents a schematic showing the sequencing for a three-vessel system using a guard bed as described above. As shown in Table 4, each of three vessels alternates its function, from adsorption to guard-bed to regeneration, spending an equal amount of time carrying out each of the three functions.

TABLE 4

| Hour | 8 | 16 | 24 |
| --- | --- | --- | --- |
| Vessel 1 | Guard | On | Regen |
| Vessel 2 | On | Regen | Guard |
| Vessel 3 | Regen | Guard | On |

While FIGS. 4A and 4B offers exemplary variations of tank arrangements for a purification/separation system in accordance with the disclosure herein, other arrangements can be envisioned to meet specifications pertaining to variables such as purity, gas flow, system size, and economics.

EXAMPLES

Example 1

Figure 5:
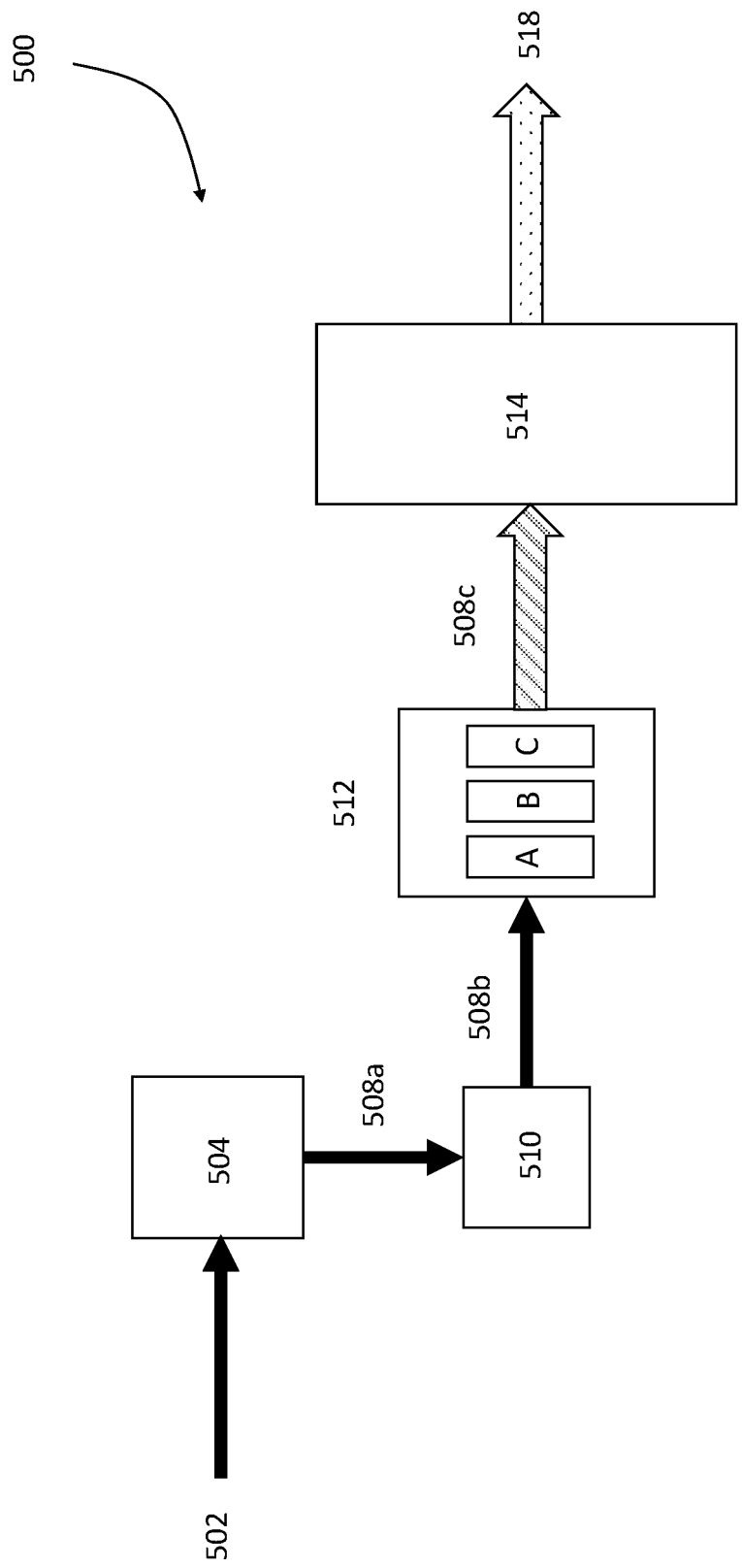
FIG. 5 is a block diagram of a purification/separation system suitable for acetylene purification.

A system for producing acetylene is shown in the block diagram of FIG. 5. FIG. 5 depicts schematically a system 500 for producing acetylene. In the depicted system 500, an inflow stream 502 is provided that contains one or more hydrocarbon precursors that can be converted into acetylene. In an embodiment, the inflow stream 502 comprises natural gas. A non-thermal plasma reactor 504 converts the hydrocarbon precursor into a plurality of hydrocarbon and non-hydrocarbon products; among the hydrocarbon products is the desired product acetylene. A product stream 508a containing the acetylene and the other hydrocarbon and non-hydrocarbon products exits the non-thermal plasma reactor 504 and passes through an optional condensables trap 510 that removes the higher-order hydrocarbons from the product stream 508a; in the absence of the condensables trap 510, the product stream 508a enters the adsorption system 510 directly. The product stream 508b that emerges from the optional condensables trap 510 then enters an adsorption system 512. In the depicted embodiment, the adsorption system 512 contains three adsorption vessels A, B, and C. The adsorption system 512 removes higher acetylenes from the product stream 508b. Following treatment in the adsorption system 512, the product stream 508c contains acetylene as the predominant hydrocarbon, along with non-hydrocarbon gases predominantly hydrogen. Minute amounts of contaminants may also reside in the product stream 508c, but the higher-order acetylenes vinylacetylene and diacetylene have been substantially removed. In one embodiment, the product stream 508c is the desirable end-product of the system for producing acetylene. In such an embodiment, the product stream 508c can be used immediately or can be combined with other gas streams for industrial purposes, such as welding, metal cutting, torch applications, and the like. In other embodiments, the product stream 508c enters a separation/purification module 516 in which acetylene can be separated from the product stream in an acetylene purifier 514 and delivered as a substantially pure acetylene gas 518. Additional features of the separation/purification module (not shown) can provide separators to purify some of the other gases in the product stream 508c, for example, hydrogen. In such an embodiment, hydrogen can be produced separately as a desirable product, along with the substantially pure acetylene gas 518.

In this Example, a system for producing acetylene is used that is similar to the block diagram of FIG. 5. In this Example, the non-thermal plasma reactor converts a natural gas inflow stream into a mixed product stream containing 87.52% hydrogen, 10.14% acetylene, 1.13% methane, 0.39% nitrogen, 0.14% ethylene, 0.01% methylacetylene, 0.55% diacetylene, 0.07% vinylacetylene, and 0.05% benzene at a flow rate of 1400 SLM. The mixed product stream then passes through subsequent purification modules, including an optional condensables trap, an adsorbent system, and an acetylene purification system, similar to those components depicted in the block diagram of FIG. 5.

Before the acetylene from the mixed product stream can be isolated in an acetylene purification system, the higher-order acetylenes (e.g., vinylacetylene and diacetylene) are removed for safety and purity considerations. Additionally, the benzene is removed to prevent fouling of the solvent in the acetylene purification system. After the mixed product stream passes through an optional condensables trap, it is directed to an adsorbent system for removal of the higher acetylenes. The adsorbent system contains three vessels, Vessel A, Vessel B, and Vessel C, similar to those vessels depicted in FIG. 5. Each vessel (Vessel A, Vessel B, Vessel C) is cylindrical in shape, 8 feet tall with 2-foot diameters and is connected in parallel via stainless-steel piping. The inlet of each vessel is centered on the circular top plate of the vessel, while the outlet is centered on the bottom plate. The vessels are able to be isolated from each other by programmable pneumatic ball valves, and each vessel is connected to parallel piping that contains the hydrogen-acetylene mixture and a separate, parallel piping system for the regeneration gas. Each vessel contains 50 gallons of an adsorbent, molecular sieve 13X, with a bed height of 2 feet centered in the middle of the vessel. The top of the adsorbent bed is 3 feet from the inlet and the bottom of the bed is 3 feet from the outlet. Above and below the bed is packing of inert, ceramic spheres with a bed height of 1 foot, respectively. The inert packing above and below the adsorbent bed is symmetrical with respect to the axial direction of the vessel. The entirety of the adsorbent and the ceramic spheres rests on a 10×10 mesh (2-micron openings) bottom support 1.5 feet above the outlet, which is held up by a grid of stainless-steel I-beams.

At the beginning of the time on stream, programmed valves open such that the hydrogen-acetylene-impurity mixture is split in half using downstream electronic pressure controllers, with each stream entering the first two vessels, called Vessel A and Vessel B, through the inlets on the top of the vessel. Meanwhile Vessel C is in standby mode, isolated from the hydrogen-acetylene-impurity flow by closed valves. The gas stream passes over the adsorbent bed in Vessels A and B for 8 hours in a downward direction. The higher acetylenes, including diacetylene, vinylacetylene, and benzene, are adsorbed onto the molecular sieve in those vessels, and the hydrogen-acetylene mixture, now purified, leaves Vessels A and B, with the outflow streams from each vessel being recombined and sent onwards for acetylene isolation in an acetylene purification system, generally as shown in FIG. 5. After 8 hours on stream, programmed valves switch on to direct the mixed product gas stream (i.e. the gas stream effluent from the optional condensables trap containing acetylene, hydrogen, and the remaining impurities) away from Vessels A+B and into Vessels B+C. Concurrently, valves switch so that Vessel A is isolated from the product gas stream, and instead is exposed to regeneration gas flowing in through a regeneration gas system (not shown in FIG. 5). In the regeneration gas system, ambient air is collected with a 60 CFM regenerative blower, passed through a 1 micron filter, and dried using a 60 CFM air chiller. The regeneration air then passes through a 20 kW inline pipe air heater where it is heated to 200° C. Once heated, the regeneration air passes through stainless-steel piping insulated with fiberglass, to enter the bottom of the vessel whose adsorbent is to be regenerated, here, Vessel A. The hot regeneration air flows upwards, countercurrent to the direction of flow for the previously-flowing product gas stream. The hot air liberates the adsorbed impurities from the adsorbent material and carries the impurities with it out of Vessel A to a vent line where the entrained impurities are incinerated in a natural gas flare stack. Once the adsorbent bed reaches a temperature of 200° C., the hot air flow is maintained for an additional 2 hours, then the air heater is turned off. The air flow no longer heated, continues to flow across the adsorbent bed as its temperature decreases; the regeneration air thus functions as a cooling gas. Vessel A is maintained as a cooling gas, and the vessel is cooled for about 4 hours, with the air flow being discontinued when the temperature inside the vessel reaches 25° C. In the final step of regeneration, Vessel A is purged of all air by introducing 500 SLM of natural gas for 30 minutes. Thereupon, Vessel A is now considered regenerated and is ready to be put back in service as an adsorption vessel.

After 16 hours on stream, Vessel B has reached full saturation and Vessel C is half-saturated. Valves switch such that the mixed products stream is directed from Vessels B+C to Vessels A+C, and Vessel B is regenerated in the same process described above. After 24 hours on stream, the mixed products stream is directed to Vessel A+B, while Vessel C is regenerated, completing a 24-hour cycle. The 24-hour cycle described in this Example can be repeated on a daily basis over a prolonged period of time. For example, this 24-hour cycle can be repeated every day for two years, or until the adsorbent in the vessels are replaced during scheduled plant maintenance.

The product stream leaving the adsorbent system described above contains 88.14% hydrogen, 10.18% acetylene, 1.14% methane, 0.39% nitrogen, 0.14% ethylene and 0.01% methylacetylene at a flow rate of 1390.2 SLM. It enters the acetylene purification system, such as is shown in FIG. 5, where the acetylene is further isolated. The gaseous product composition leaving the acetylene purification system includes 99.6% acetylene, 0.2% ethylene, 0.1% hydrogen, and 0.1% methylacetylene, with <1 ppm of diacetylene and <1 ppm of vinylacetylene, at a flow rate of 141.0 SLM.

Example 2

A small-scale, non-thermal plasma reactor system, similar to that depicted in the block diagram of FIG. 5 and described above, converts propane into a mixed product stream containing 72.4% hydrogen, 15.3% acetylene, 0.5% diacetylene, 0.1% vinylacetylene, 0.1% methylacetylene, and 0.1% benzene, at a flow rate of 15 SLM. Before the hydrogen and acetylene in the mixed product stream can be used in an oxyfuel torch for steel fabrication and cutting, the impurities must be removed to create a uniform cutting flame.

The mixed product stream is directed to a 2-vessel adsorption system for impurity removal. The vessels are 6 inches tall with 3" diameters, and are packed with 300 grams of 13X molecule sieve. The molecular sieve is held in the center of the vessel using 3 micron ceramic wool packing throughout the entirely of the vessel. The adsorption system operates in a continuous fashion, whereby the mixed product stream is scrubbed in one vessel for 8 hours on stream, while the other vessel is regenerated with 15 SLM of 200° C. dry air for 2 hours before being cooled to room temperature with 15 SLM of room temperature, dry air. The two vessels switch back and forth between adsorption and regeneration every 8 hours on stream. An integrated, hardware programmable logic controller PLC program logs the hours on stream and switches the two vessels between adsorption and regeneration when 8 hours on stream has been reached. The adsorbent vessel is replaced after 8,000 hours of use, or 1000 cycles.

While this invention has been particularly shown and described with references to preferred embodiments thereof, it will be understood by those skilled in the art that various changes in form and details may be made therein without departing from the scope of the invention encompassed by the appended claims. Unless otherwise indicated, all numbers expressing reaction conditions, quantities, amounts, ranges and so forth, as used in this specification and the claims are to be understood as being modified in all instances by the term "about." Accordingly, unless indicated to the contrary, the numerical parameters set forth herein are approximations that can vary depending upon the desired properties sought to be obtained by the present invention.

What is claimed:

1. A method for removing higher acetylenes from a gaseous stream comprising a hydrogen fraction and a non-hydrogen fraction, wherein the gaseous stream comprises less than about 4% in total of diacetylene and vinylacetylene, the method comprising:
    an adsorption step comprising passing the gaseous stream at a preselected superficial linear gas velocity across an adsorption bed supported within an enclosure, the adsorption bed containing a crystalline porous ceramic adsorbent to adsorb the higher acetylenes onto the adsorbent, thereby producing a saturated adsorption bed and a purified gaseous stream comprising less than about 25 ppm of diacetylene and less than about 25 ppm of vinylacetylene;
    a regeneration step comprising regenerating the saturated adsorbent bed by passing a regeneration gas across the saturated adsorption bed to desorb the higher acetylenes retained thereupon, thereby producing a regenerated adsorbent bed and a contaminated gas stream bearing the higher acetylenes, and
    a purging step, comprising removing the contaminated gas stream from the enclosure.

2. The method of claim 1, wherein the gaseous stream comprises between about 50% and about 90% hydrogen.

3. The method of claim 2, wherein the non-hydrogen fraction of the gaseous stream comprises greater than about 50% alkynes.

4. The method of claim 2, wherein the non-hydrogen fraction of the gaseous stream comprises between about 5% and about 95% acetylene.

5. The method of claim 2, wherein the non-hydrogen fraction of the gaseous stream comprises between about 80% and about 90% acetylene.

6. The method of claim 1, wherein the gaseous stream comprises less than about 2% of diacetylene or less than about 2% of vinylacetylene, or wherein the gaseous stream comprises less than about 2% of diacetylene and less than about 2% of vinylacetylene.

7. The method of claim 1, wherein the gaseous stream is directed in a flow direction that is axial to the adsorption bed.

8. The method of claim 1, wherein the crystalline porous ceramic adsorbent has a surface area greater than 200 $m^2/g$, and pore diameters greater than 0.5 nm.

9. The method of claim 1, wherein the crystalline porous ceramic adsorbent is a 13X molecular sieve.

10. The method of claim 1, wherein the purified gaseous stream comprises less than about 20 ppm of diacetylene.

11. The method of claim 1, wherein the purified gaseous stream comprises less than about 20 ppm of vinylacetylene.

12. The method of claim 10, wherein the purified gaseous stream comprises less than about 10 ppm of diacetylene.

13. The method of claim 11, wherein the purified gaseous stream comprises less than about 10 ppm of vinylacetylene.

14. The method of claim 1, wherein the regeneration gas is heated hot air.

15. The method of claim 14, wherein the heated hot air has a temperature between about 175° C. and about 200° C.

16. The method of claim 14, wherein the heated hot air has a temperature of about 200° C. or higher.

17. The method of claim 1, wherein the purging step further comprises exposing the adsorbent bed in the enclosure to a purge gas.

18. The method of claim 1, wherein performance of the purge step is followed by subsequent performance of the adsorption step, the regeneration step and the purge step, for a preselected number of performance cycles.

19. The method of claim 18, wherein the adsorption step is performed in a first enclosing vessel while the regeneration step and the purge step are performed in a second enclosing vessel, with cycling between the adsorption step in one vessel and the regeneration and purge steps in the other vessel for a preselected number of performance cycles.

20. The method of claim 1, further comprising an initial step wherein the gaseous stream is produced by exposing a feed gas comprising a $C_1$-$C_4$ hydrocarbon to an energy source to transform the feed gas into a plasma, wherein the plasma effects conversion of the $C_1$-$C_4$ hydrocarbon into the hydrogen fraction and the non-hydrogen fraction of the gaseous stream.

21. The method of claim 20, wherein the feed gas comprises methane.

22. The method of claim 21, wherein the plasma is a non-thermal plasma.

23. A system for removing diacetylene and vinylacetylene from a hydrogen-dominant acetylene-hydrogen gaseous stream, wherein the hydrogen-dominant acetylene-hydrogen gaseous stream comprises less than one percent each of diacetylene and vinylacetylene, the system comprising:

- a first vessel comprising a first adsorbent bed supported in a direction that is transverse to a long axis of the first vessel;
- a first process gas circuit in fluid communication with the first vessel, comprising a process gas inflow line entering the first vessel through a process gas inlet upstream of the first adsorbent bed for inflow of the hydrogen-dominant acetylene-hydrogen gaseous stream, and further comprising a purified-gas outlet downstream from the first adsorbent bed for outflow of a purified gaseous stream from the first vessel, wherein the hydrogen-dominant acetylene-hydrogen gaseous stream containing diacetylene and vinylacetylene enters the process gas inlet and passes across the first adsorption bed, wherein the diacetylene and vinylacetylene are adsorbed onto the first adsorbent bed to form a first saturated adsorbent bed, and wherein the purified gaseous stream exiting the purified-gas outlet contains less than about 25 ppm each of the diacetylene and vinylacetylene, said first process gas circuit possessing a first set of control valves proximal and distal to the first vessel, the first set of control valves being programmed to permit or prevent flow of process gas through the first process gas circuit; and
- a first regeneration gas circuit in fluid communication with the first vessel, comprising a regeneration gas line entering the first vessel through a regeneration gas inlet at a first end of the first adsorbent bed for inflow of a regeneration gas, and a regeneration gas outlet exiting the first vessel at a second end of the first adsorbent bed for outflow of a contaminated regeneration gas, wherein the regeneration gas passes across the first saturated adsorption bed from the first end to the second end thereof, and wherein the regeneration gas desorbs the diacetylene and vinylacetylene contaminants from the first saturated adsorption bed in transit across thereof to form the contaminated regeneration gas, said first regeneration gas circuit possessing a second set of control valves, the second set of control valves being programmed to permit or prevent flow of regeneration gas through the first regeneration gas circuit;

wherein, when gas is flowing through the first process gas circuit across the first adsorption bed, no gas is flowing through the first regeneration gas circuit across the first adsorption bed, and wherein when gas is flowing through the first regeneration gas circuit across the first adsorption bed, no gas is flowing through the first process gas circuit.

24. The system of claim 23, further comprising:
- a second vessel identical to the first vessel and having a second adsorption bed;
- a second process gas circuit identical to the first process gas circuit and in fluid communication with the first process gas circuit and the second vessel; and
- a second regeneration gas circuit identical to the first regeneration gas circuit and in fluid communication with the first regeneration gas circuit and the second vessel, wherein, when gas is flowing through the first process gas circuit across the first adsorption bed in the first vessel, regeneration gas is flowing through the second regeneration gas circuit across the second adsorption bed in the second vessel.

* * * * *